United States Patent

Keshwani

(10) Patent No.: US 11,823,375 B2
(45) Date of Patent: Nov. 21, 2023

(54) MACHINE LEARNING DEVICE AND METHOD

(71) Applicant: FUJIFILM Corporation, Tokyo (JP)

(72) Inventor: Deepak Keshwani, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 695 days.

(21) Appl. No.: 17/017,647

(22) Filed: Sep. 10, 2020

(65) Prior Publication Data

US 2020/0410677 A1 Dec. 31, 2020

Related U.S. Application Data

(63) Continuation of application No. PCT/JP2019/009479, filed on Mar. 8, 2019.

(30) Foreign Application Priority Data

Mar. 16, 2018 (JP) ................................. 2018-049905

(51) Int. Cl.
*G06T 7/00* (2017.01)
*G06F 16/18* (2019.01)
(Continued)

(52) U.S. Cl.
CPC ............ *G06T 7/0012* (2013.01); *G06F 16/18* (2019.01); *G06N 3/048* (2023.01); *G06N 20/00* (2019.01);
(Continued)

(58) Field of Classification Search
CPC ......... G06T 7/0012; G06T 2207/10072; G06T 2207/20081; G06T 2207/20084; G06F 16/18; G06N 20/00; G06N 3/048
See application file for complete search history.

(56) References Cited

U.S. PATENT DOCUMENTS

2017/0061330 A1 3/2017 Kurata
2018/0307946 A1* 10/2018 Kuroda .................. G06F 16/48
(Continued)

FOREIGN PATENT DOCUMENTS

CA 2850189 A1 * 3/2013 ........... A61B 17/083
CN 105009171 A * 10/2015 ............... G06K 9/34
(Continued)

OTHER PUBLICATIONS

"Office Action of Japan Counterpart Application", dated Jul. 30, 2021, with English translation thereof, p. 1-p. 6.
(Continued)

Primary Examiner — Khai M Nguyen
(74) Attorney, Agent, or Firm — JCIPRNET

(57) ABSTRACT

Provided are a machine learning device and a method capable of performing machine learning of labeling for accurately attaching a plurality of labels to volume data at once by using learning data with mixed inconsistent labeling. A neural network (14) receives an input of multi-slice images of learning data Di (i=1, 2, . . . n) of which a class to be labeled is n types, and creates a prediction mask of n anatomical structures i by a convolutional neural network (CNN) or the like (S1). A machine learning unit (13) calculates a prediction accuracy acc(i) of the class corresponding to the learning data Di for each learning data Di (S2). The machine learning unit (13) calculates a weighted average M of an error di between the prediction accuracy acc(i) and a ground truth mask Gi. The machine learning unit (13) calculates a learning loss by a loss function Loss (S4). The machine learning unit (13) changes each coupling load of the neural network (14) from an output layer side to an input layer side according to a value of the learning loss calculated by the loss function Loss (S5).

11 Claims, 7 Drawing Sheets

(51) Int. Cl.
    *G06N 20/00*     (2019.01)
    *G06N 3/048*     (2023.01)

(52) U.S. Cl.
    CPC ............... *G06T 2207/10072* (2013.01); *G06T 2207/20081* (2013.01); *G06T 2207/20084* (2013.01)

(56) References Cited

U.S. PATENT DOCUMENTS

| | | | | |
|---|---|---|---|---|
| 2019/0034800 | A1* | 1/2019 | Shiratani | G06N 3/042 |
| 2020/0387751 | A1* | 12/2020 | Keshwani | G06V 10/764 |

FOREIGN PATENT DOCUMENTS

| | | | | |
|---|---|---|---|---|
| CN | 107220980 A | * | 9/2017 | ........... G06N 3/0454 |
| JP | 2017049684 | | 3/2017 | |
| WO | 2017073373 | | 5/2017 | |
| WO | 2017175282 | | 10/2017 | |

OTHER PUBLICATIONS

"International Search Report (Form PCT/ISA/210) of PCT/JP2019/009479," dated May 28, 2019, with English translation thereof, pp. 1-5.

"Written Opinion of the International Searching Authority (Form PCT/ISA/237) of PCT/JP2019/009479," dated May 28, 2019, with English translation thereof, pp. 1-10.

Jonathan Long, et al., "Fully Convolutional Networks for Semantic Segmentation," Mar. 2015, pp. 1-10, available at https://arxiv.org/pdf/1411.4038.pdf.

Fausto Milletari, et al., "V-Net: Fully Convolutional Neural Networks for Volumetric Medical Image Segmentation," Jun. 2016, pp. 1-11, available at https://arxiv.org/pdf/1606.04797.pdf.

Kanehira, Atsushi, et al., "Multi-label classification problem caused by incomplete labeled data," IPSJ SIG Technical Report, with concise English explanation of relevance in the Written Opinion of the International Searching Authority (Form PCT/ISA/237) of PCT/JP2019/009479, Nov. 2015, pp. 1-8.

Yunchao Wei, et al., "CNN: Single-label to Multi-label," Jul. 2014, pp. 1-14, available at https://arxiv.org/pdf/1406.5726.pdf.

Kenta Oono, "What design would there applied if there were multiple correct answer label," with concise English explanation of relevance in the Written Opinion of the International Searching Authority (Form PCT/ISA/237) of PCT/JP2019/009479, accessed May 2019, pp. 1-2, available at https://groups.google.com/forum/#!msg/chainer/1VmC3PINZ8U/r5BunA-XCQAJ.

Tong Shen, et al., "Learning Multi-level Region Consistency with Dense Multi-label Networks for Semantic Segmentation," Proceedings of the Twenty-Sixth International Joint Conference on Artificial Intelligence (IJCAI-17), Jan. 2017, pp. 2708-2714.

Yunchao Gong, et al., "Deep Convolutional Ranking for Multilabel Image Annotation," Apr. 2014, pp. 1-9, available at https://arxiv.org/pdf/1312.4894.pdf.

Md Atiqur Rahman, et al., "Optimizing Intersection-Over-Union in Deep Neural Networks for Image Segmentation," International Symposium on Visual Computing 2016 (ISVC2016): Advances in Visual Computing, Dec. 2016, pp. 1-12.

* cited by examiner

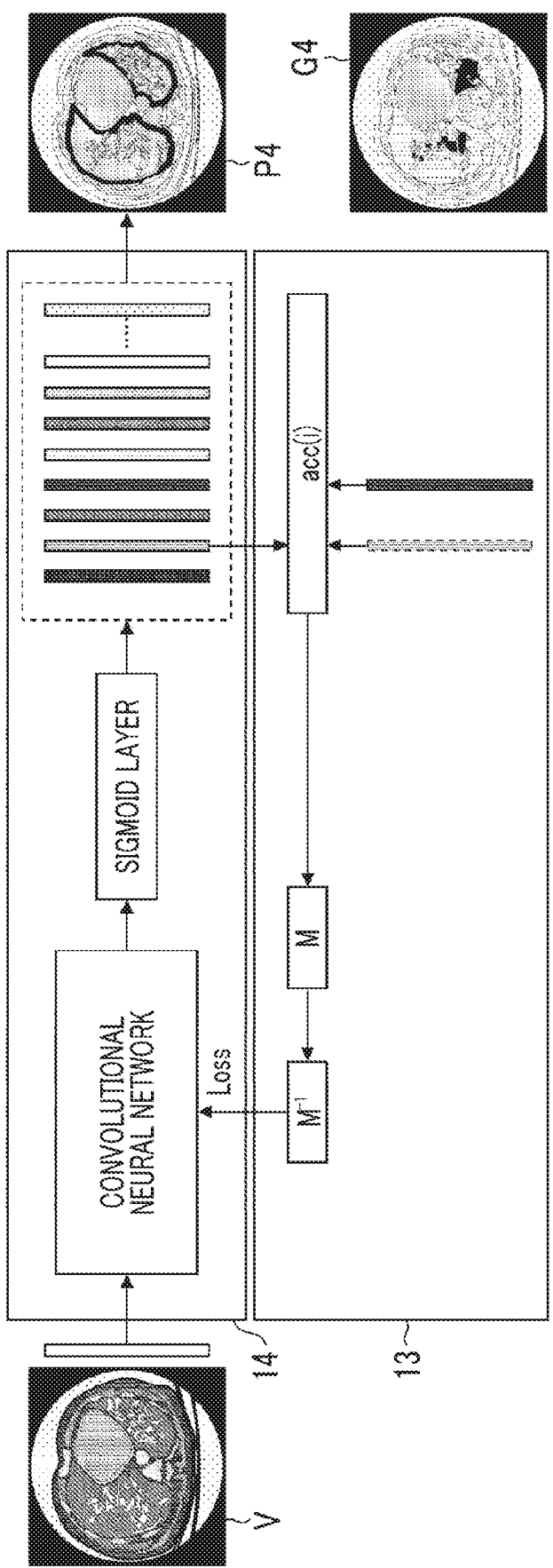

MACHINE LEARNING DEVICE AND METHOD

CROSS-REFERENCE TO RELATED APPLICATIONS

The present application is a Continuation of PCT International Application No. PCT/JP2019/009479 filed on Mar. 8, 2019 claiming priority under 35 U.S.C § 119(a) to Japanese Patent Application No. 2018-049905 filed on Mar. 16, 2018. Each of the above applications is hereby expressly incorporated by reference, in its entirety, into the present application.

BACKGROUND OF THE INVENTION

1. Field of the Invention

The present invention relates to a machine learning device and a method, and particularly relates to a machine learning device and a method for constructing a machine learning model for classifying (segmenting) a structure of an image.

2. Description of the Related Art

In the related art, there is a learned model for determining which of a plurality of labels each pixel value belongs to, for three-dimensional medical image data (volume data) such as a computed tomography (CT) image.

For example, in Jonathan Long, Evan Shelhamer, Trevor Darrell, UC Berkeley "Fully Convolutional Networks for Semantic Segmentation", Internet <URL https://arxiv.org/pdf/1411.4038.pdf, disclosed is a technique for adjusting contribution of erroneous segmentation for large and small features by computing a normalized probability mask using a softmax layer at an end of a neural network and computing a learning loss with weighted cross entropy regarding image segmentation.

In Fausto Milletari, Nassir Navab, Seyed-Ahmad Ahmadi, "V-Net: Fully Convolutional Neural Networks for Volumetric Medical Image Segmentation", Internet <URL https://arxiv.org/pdf/1606.04797.pdf>, a learning model for simultaneously determining (labeling) which of "lung", "brain", "liver", "rib", "spine", "fat", and "the other" each voxel belongs to in a case where a three-dimensional CT image is input is proposed.

SUMMARY OF THE INVENTION

It is extremely difficult to prepare learning data in which a plurality of labels are attached to each voxel of the three-dimensional CT image in order to allow such a learning model to be learned, mainly from a viewpoint of effort.

In a case where pieces of learning data with a label of a single organ attached thereto, such as learning data with a ground truth label of only "lung" attached thereto and learning data with a ground truth label of only "brain" attached thereto, are obtained and brought together to be used as learning data for labeling a plurality of organs, the effort therefor is small.

However, in this case, for example, in a case where ground truth labels of "lung" and "lung bronchus" are obtained, learning data in which only the label of "lung" is attached to a voxel of "lung bronchus" and learning data in which only the label of "lung bronchus" is attached to a voxel of "lung bronchus" may be mixed.

According to the technique of Jonathan Long, Evan Shelhamer, Trevor Darrell, UC Berkeley "Fully Convolutional Networks for Semantic Segmentation", Internet <URL https://arxiv.org/pdf/1411.4038.pdf, only one label can be attached to each pixel. In addition, adjustment of contribution of large and small features to segmentation by computing a learning loss with weighted cross entropy may result in exaggerated segmentation from small features. Furthermore, according to the technique of Fausto Milletari, Nassir Navab, Seyed-Ahmad Ahmadi, "V-Net: Fully Convolutional Neural Networks for Volumetric Medical Image Segmentation", Internet <URL https://arxiv.org/pdf/1606.04797.pdf>, since a normalized probability mask is computed using a softmax function in a final layer of a neural network, a set of pieces of data with a single label inconsistently and separately attached thereto cannot be used as learning data.

An object of the present invention is to provide a machine learning device and a method capable of performing machine learning of labeling for accurately attaching a plurality of labels to volume data at once by using learning data with mixed inconsistent labeling.

A machine learning device according to a first aspect of the present invention comprises: a first learning data input unit that receives an input of first learning data including volume data of a tomographic image and a ground truth label of a first class in the volume data; a second learning data input unit that receives an input of second learning data including the volume data and a ground truth label of a second class different from the first class in the volume data; a prediction label creation unit that, by a neural network, creates a prediction label of the first class from the volume data of the first learning data whose input is received by the first learning data input unit, and creates a prediction label of the second class independent of the prediction label of the first class from the volume data of the second learning data whose input is received by the second learning data input unit; an integrated error calculation unit that calculates an integrated error between an error between the prediction label of the first class and the ground truth label of the first class and an error between the prediction label of the second class and the ground truth label of the second class by weighted averaging; and a machine learning unit that causes the neural network to perform machine learning to create the prediction labels of both a label of the first class and a label of the second class in the volume data based on the integrated error calculated by the integrated error calculation unit.

In the machine learning device according to a second aspect of the present invention, the integrated error calculation unit calculates the integrated error based on an intersection over union (IoU) between the prediction label of the first class and the ground truth label of the first class and an intersection over union (IoU) between the prediction label of the second class and the ground truth label of the second class.

In the machine learning device according to a third aspect of the present invention, the integrated error calculation unit calculates a detection accuracy based on a Dice coefficient between the prediction label of the first class and the ground truth label of the first class and a Dice coefficient between the prediction label of the second class and the ground truth label of the second class.

In the machine learning device according to a fourth aspect of the present invention, the prediction label of the first class and the prediction label of the second class are created based on a sigmoid function.

In the machine learning device according to a fifth aspect of the present invention, the tomographic image is a three-dimensional medical tomographic image, and the first class and the second class include an anatomical structure.

In the machine learning device according to a sixth aspect of the present invention, the integrated error calculation unit creates the ground truth label of the second class from the ground truth label of the first class based on relevance data indicating a relationship on an anatomical system between the first class and the second class, and then calculates the integrated error between the error between the prediction label of the first class and the ground truth label of the first class and the error between the prediction label of the second class and the ground truth label of the second class.

In the machine learning device according to a seventh aspect of the present invention, the second class is in an anatomically upper rank than the first class in the relevance data.

In a machine learning method according to an eighth aspect of the present invention, the method executed by a computer comprises: a step of receiving an input of first learning data including volume data of a tomographic image and a ground truth label of a first class in the volume data; a step of receiving an input of second learning data including the volume data and a ground truth label of a second class different from the first class in the volume data; a step of, by a neural network, creating a prediction label of the first class from the volume data of the first learning data and creating a prediction label of the second class independent of the prediction label of the first class from the volume data of the second learning data; a step of calculating an integrated error between an error between the prediction label of the first class and the ground truth label of the first class and an error between the prediction label of the second class and the ground truth label of the second class by weighted averaging; and a step of causing the neural network to perform machine learning to create the prediction labels of both a label of the first class and a label of the second class in the volume data based on the integrated error.

The present invention also includes a machine learning program for causing a computer to execute this machine learning method, and a machine-learned model that is machine-learned by the machine learning program. Furthermore, the present invention also includes a non-transitory computer-readable recording medium for causing a computer to execute the machine learning program in a case where instructions stored in the recording medium are read by the computer.

According to the present invention, it is possible to perform machine learning by calculating an integrated error for a first class and a second class for which prediction errors are independently calculated, and it is possible to perform multi-labeling machine learning using non-multi-labeled learning data.

BRIEF DESCRIPTION OF THE DRAWINGS

FIG. 7 is a diagram illustrating a concept of backpropagation according to a prediction class (blood vessel).

DESCRIPTION OF THE PREFERRED EMBODIMENTS

Figure 1:
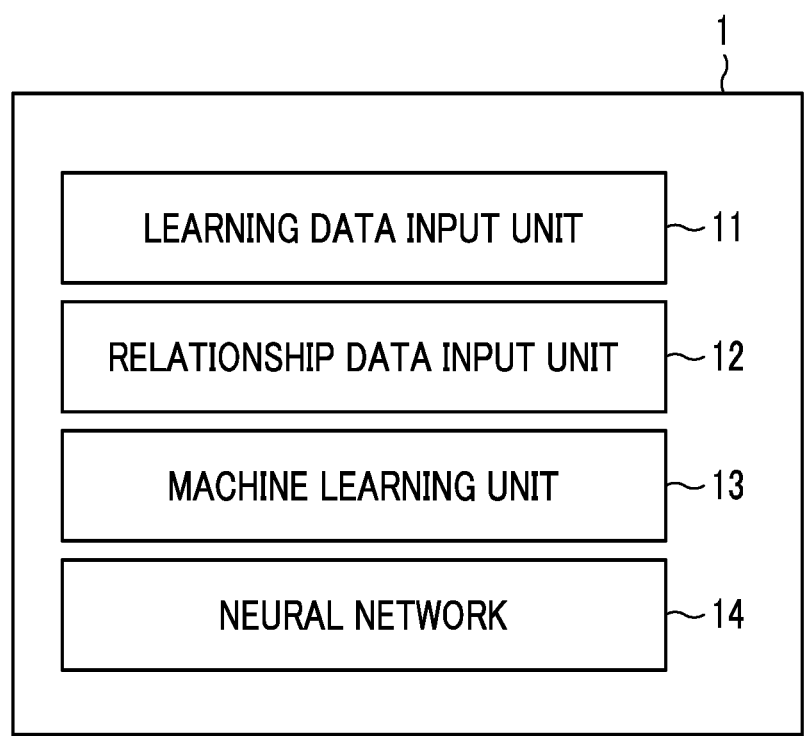
FIG. 1 is a schematic configuration diagram of a machine learning data creation device.

FIG. 1 is a schematic configuration diagram of a machine learning device 1 according to a preferred embodiment of the present invention. The machine learning device 1 comprises a learning data input unit 11, a relationship data input unit 12, a machine learning unit 13, and a neural network 14. The machine learning device 1 is configured by a computer comprising a processor such as a graphics processing unit (GPU), and each of the above units is realized by a program executed by the processor. The machine learning device 1 may or may not include the neural network 14.

The learning data input unit 11 receives an input of a set (learning data) of volume data including volume data including a large number of axial tomographic images (multi-slice images) and a ground truth mask in which each pixel in the image is classified into a type (class) of an anatomical structure by manually attaching (labeling) a ground truth label such as "lung", "bronchus", "blood vessel", "air filled pattern", or "others (background)" to each voxel included in the volume data by a doctor or the like.

In the ground truth mask of the learning data, at least one type of labeling may be present on a voxel, and a plurality of types of labeling may or may not be present on one voxel. For simplification of explanation, it is assumed that each voxel of the learning data input to the learning data input unit 11 is attached with "others" or one label other than "others". Hereinafter, this is referred to as single labeling.

For example, each voxel of a ground truth mask of learning data A is attached with a label of "lung" or "others", each voxel of a ground truth mask of learning data B different from the learning data A is attached with a label of "bronchus" or "others", and each voxel of a ground truth mask of learning data C different from the learning data A and the learning data B is attached with a label of "blood vessel" or "others". The learning data input unit 11 receives learning data including the pieces of learning data A, B, and C in which targets of single labeling are different (that is, the targets of single labeling are independent of each other). However, different types of single labeling may be assigned to different voxels of one ground truth mask. For example, a certain voxel of one ground truth mask may be attached with a label of "bronchus", and another voxel of the same ground truth mask may be attached with a label of "blood vessel".

The relationship data input unit 12 receives an input of relationship data indicating a relationship between voxel groups, that is, classes of volume data after being subjected to single labeling by the neural network 14.

The machine learning unit 13 causes the neural network 14 to perform machine learning based on the learning data input to the learning data input unit 11 and the structural relationship data input to the relationship data input unit 12.

The neural network 14 is a multi-layer classifier configured by a convolutional neural network (CNN) and a sigmoid layer. The neural network 14 classifies a structure in the image into each class by attaching a label such as "lung", "bronchus", "blood vessel", "air filled pattern", or "others (background)" to each voxel of the input image according to a model machine-learned by the machine learning unit 13.

The neural network 14 can perform a plurality of types of labeling of two or more for each voxel. For example, the neural network 14 can perform labeling for a certain voxel with "bronchus" and "lung".

Figure 2:
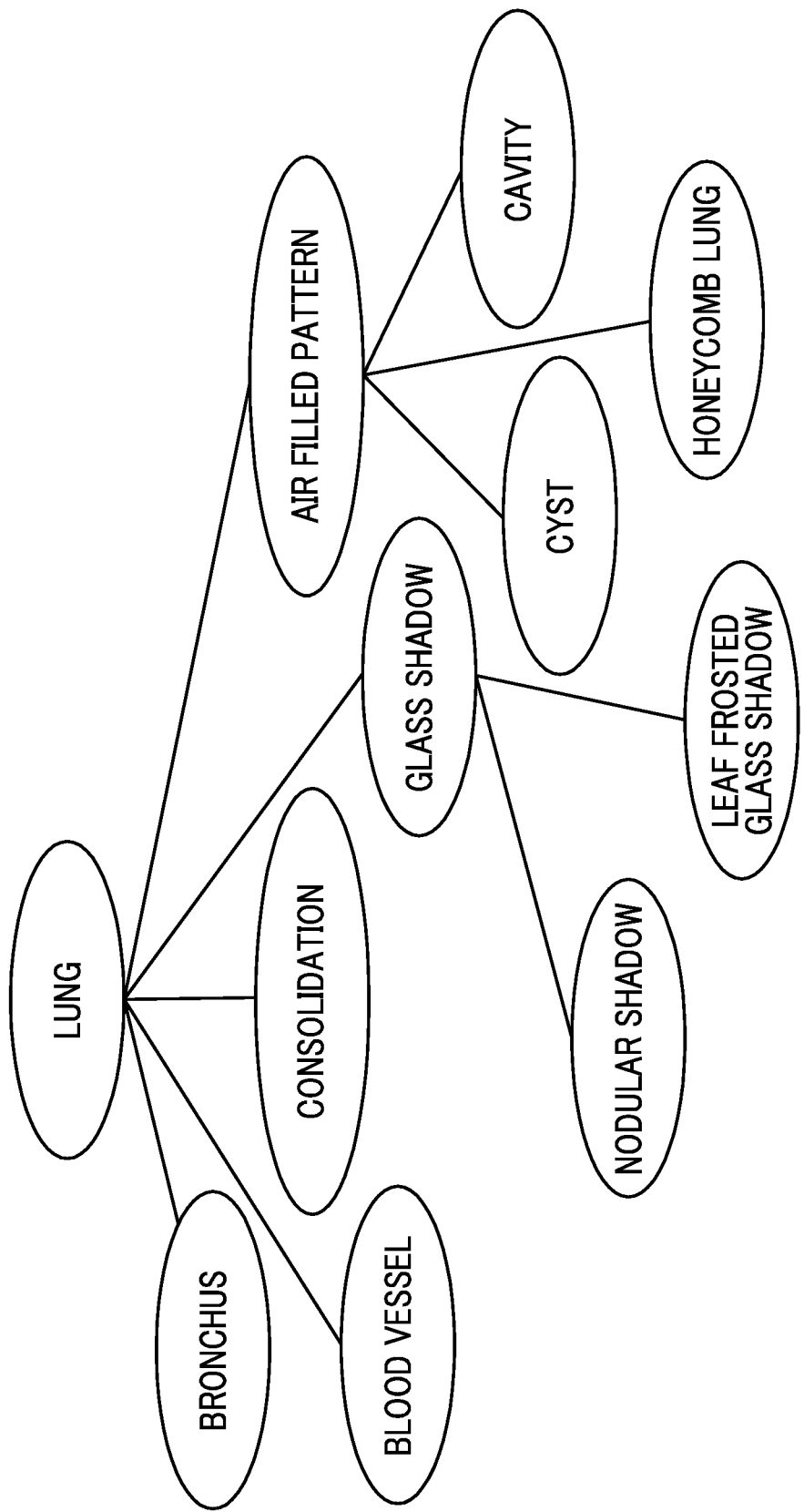
FIG. 2 is a conceptual explanatory diagram of relationship data.

FIG. 2 is an example of the relationship data. The relationship data shows a relationship between classes in a hierarchical structure. For example, as an anatomical structure of a lower hierarchy related to a class of "lung", there are classes such as "blood vessel", "consolidation (a state in which the alveoli are replaced by something other than air, such as a center of inflammation, and the lung is hard)", "glass shadow", "air filled pattern", and "bronchus".

In addition, as an anatomical structure of a lower hierarchy related to a class of "glass shadow", there are classes of "nodular shadow" and "leaf frosted glass shadow".

In addition, as an anatomical structure of a lower hierarchy related to a class of "air filled pattern", there are classes of "cyst", "honeycomb lung", and "cavity".

This hierarchical relationship shows an anatomical inclusion relationship between classes. For example, "nodular shadow" is included in "glass shadow", and "glass shadow" is included in "lung". Therefore, all of the types of labeling of "nodular shadow", glass shadow", and "lung" can be learned from a ground truth mask of a voxel attached with a label of "nodular shadow".

The hierarchical structure in the relationship data needs not be a parent-child relationship. For example, metastasis is located in a lower hierarchy of "bronchus" and "lymph node", but there may be no hierarchical relationship between "bronchus" and "lymph node".

Figure 3:
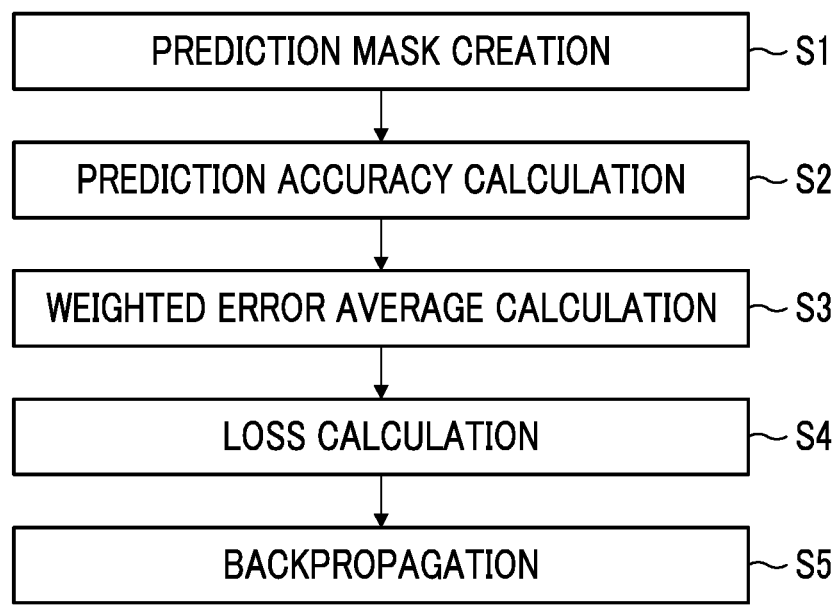
FIG. 3 is a flowchart of a machine learning process.

FIG. 3 is a flowchart of a machine learning process. A program for causing the processor of the machine learning device 1 to execute the machine learning process is stored in a computer-readable tangible storage medium such as a random access memory (RAM) of the machine learning device 1.

First, in S1 (prediction mask creation step), the neural network 14 receives an input of multi-slice images of learning data Di (i=1, 2, . . . n) of which a class to be labeled is n types, and creates a prediction mask (a set of voxel groups classified into each class by the neural network 14) of n anatomical structures i by a convolutional neural network or the like. The prediction mask and the ground truth mask may be displayed on a display screen by volume rendering.

In S2 (prediction accuracy calculation step), the machine learning unit 13 calculates a prediction accuracy acc(i) (a value indicating a certainty of labeling) of a class Ci corresponding to a voxel of the learning data Di for each learning data Di. The prediction accuracy acc(i) is represented by the following sigmoid function and takes a value between 0 and 1.

$$acc(i)=1/\{1+\exp(-vi)\}$$

vi is a logit.

Since the neural network 14 is capable of performing multi-labeling, a certainty of multi-labeling of each class for the input voxel can be obtained by a softmax function using a softmax layer. This is called a soft label. However, in the present embodiment, since the ground truth mask is single-labeled, the soft label cannot be calculated. Therefore, an independent prediction accuracy acc(i) of each class Ci is obtained by using a sigmoid function indicating a certainty of binary classification as to whether the input voxel is the class Ci or not.

In S3 (weighted error average calculation step), the machine learning unit 13 calculates, from the prediction accuracy acc(i) of the class Ci corresponding to one voxel of the learning data Di and a ground truth mask Gi corresponding to the voxel, a weighted average M of an error di between the prediction accuracy acc(i) of the class of the voxel and the ground truth mask Gi.

A weight αi of the error di is a Dice coefficient. That is, assuming that a set of class prediction results obtained by machine learning for each voxel of the learning data Di is Pr(i), a set of ground truth masks of the class Ci of the learning data Di is Ht, the number of voxels in an intersection of Pr(i) and Ht is Bi, the number of voxels in Pr(i) is Ai+Bi, the number of voxels in Ht is Bi+Ci, a weight is w (w is 1 or more), and the total number of classes is n, definition by the following formula is made.

$$\alpha i = w*Bi/(Ai+w*Bi+Ci)$$

$$M = \Sigma \alpha i di / n$$

The error di is defined by a known optional error such as a square error or an absolute value error. For example, in a case where the error di is a square error, assuming that prediction of the machine learning matches the ground truth mask (ground truth), the error di is 0, and assuming that prediction does not match the ground truth mask (no ground truth), the error di is a value equal to or less than 1 according to a degree of mismatch. By appropriately adjusting the weight αi, an influence of a size of the anatomical structure on the learning can be removed.

A+B+C is the number of voxels in a union of Pr(i) and Ht. Therefore, in a case where w=1, αi is an intersection over union (IoU). As a prediction accuracy of the class Ci increases, α(i) approaches 1. In a case where Bi=0, αi=0. That is, for a class for which a ground truth is not defined in the ground truth mask in the first place, an error regarding prediction of this class is ignored in calculation of the weighted average M. For example, even in a case where "lung" is predicted for a certain voxel, assuming that a label of "lung" is not given to the voxel in the ground truth mask, the weight αi corresponding to the error di of "lung" is 0, and the error di of "lung" does not affect a value of a weighted average S.

On the other hand, in a case where a class of "lung" and a class of "air filled pattern" are independently predicted for a certain voxel, assuming that labels of "lung" and "air filled pattern" are given to the voxel in the ground truth mask, a weight α1 corresponding to an error d1 of "lung" and a weight α2 corresponding to an error d2 of "air filled pattern" are not 0. In this case, both values of the error d1 and the error d2 are reflected in the value of S according to values of the weights α1 and α2.

However, in the relationship data, for an anatomical structure in an upper rank than the anatomical structure of the ground truth mask, an error is not ignored even in a class for which a ground truth is not defined in the ground truth mask. For example, in a case where "lung" and "bronchus" are independently predicted for a certain voxel and only a label of "bronchus" is defined in the ground truth mask of the voxel, a ground truth label of "lung" is given to the voxel in a pseudo manner, and then the weighted average M of an error of "lung" and an error of "bronchus" is calculated. This is because "lung" is an upper-rank anatomical structure including "bronchus", and therefore, in a case where labeling of "bronchus" is a ground truth, labeling of "lung" is naturally a ground truth. In this way, by giving a ground truth label in a pseudo manner according to the hierarchical relationship of the anatomical structure, it is possible to save the trouble of preparing a ground truth for multi-labeling in advance.

However, a calculation formula of a detection accuracy is not limited to the above. In general, it can be expressed by the following formula.

$$acc(i)=f1(Pr(i) \cap Ht)/f2(Pr(i) \cup Ht)$$

f1 is a function using the following formula as a parameter.

$$Pr(i) \cap Ht$$

f2 is a function using the following formula as a parameter.

$$Pr(i) \cup Ht$$

In S3 (loss calculation step), the machine learning unit 13 calculates a learning loss using a loss function Loss.

Here, the loss function Loss is defined by a reciprocal of the weighted average M. However, a formula of the loss function is not limited to the above.

In S4 (backpropagation step), the machine learning unit 13 changes each coupling load of the neural network 14 from an output layer side to an input layer side according to a value of the learning loss calculated by the loss function Loss. S1 to S4 described above can be repeated any number of times. Therefore, the coupling load of the neural network 14 is updated such that the loss for both the class defined by the ground truth mask and the class of the anatomical structure in an upper rank than the class is minimized. As a result, multi-labeling machine learning based on the ground truth mask for single labeling and a machine-learned model capable of performing multi-labeling by the machine learning are obtained.

FIGS. 4 to 7 are diagrams each illustrating a concept of backpropagation according to the prediction class.

Figure 4:
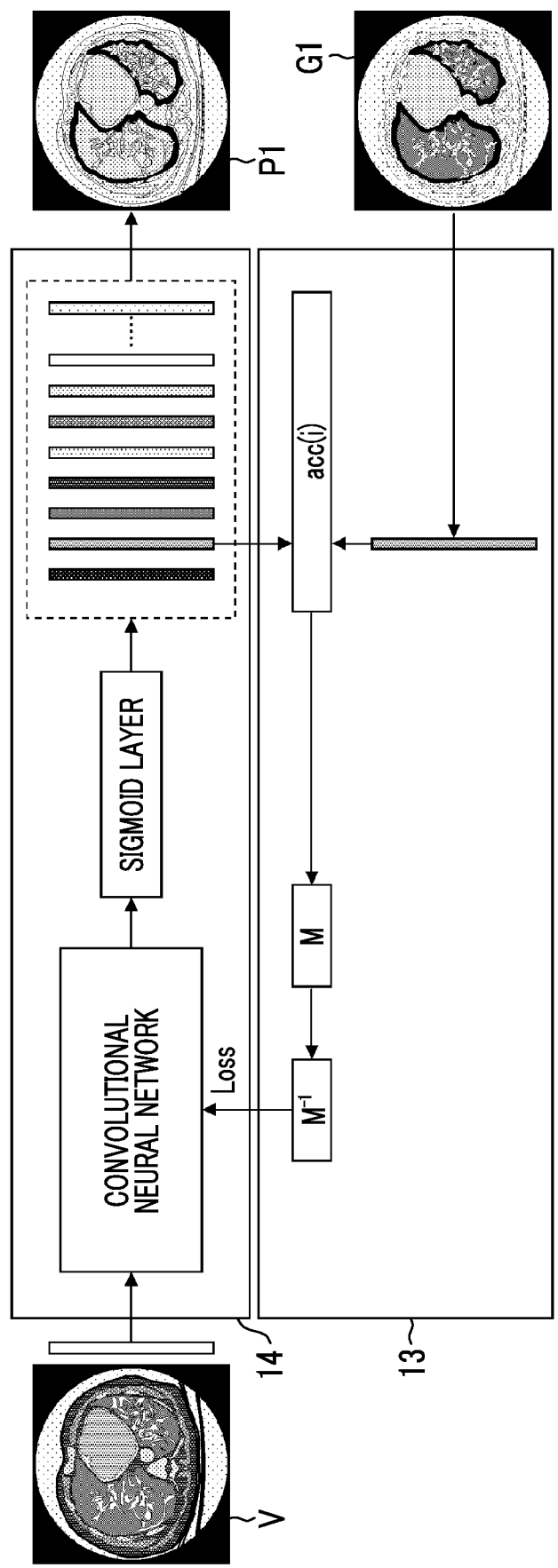
FIG. 4 is a diagram illustrating a concept of backpropagation according to a prediction class (lung).

Among these, FIG. 4 shows backpropagation due to a learning loss between a ground truth mask G1 of "lung" and a prediction mask P1 of "lung" predicted from volume data V. In this case, backpropagation is performed in which only a learning loss of "lung" is considered.

Figure 5:
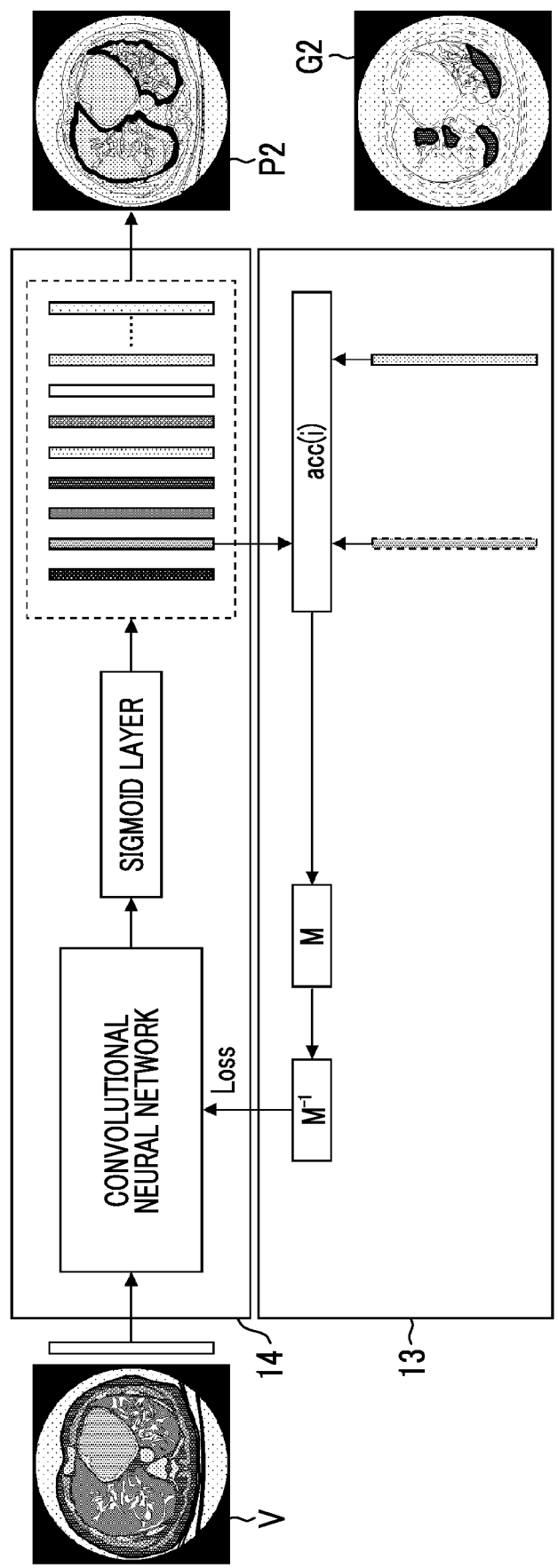
FIG. 5 is a diagram illustrating a concept of backpropagation according to a prediction class (honeycomb lung).

FIG. 5 shows backpropagation due to a learning loss between a ground truth mask G2 of "honeycomb lung" and a prediction mask P2 of "honeycomb lung" predicted from the volume data V. In this case, backpropagation is performed in which both (or either one) of a learning loss of "honeycomb lung" and learning losses of "air filled pattern" and "lung" of the anatomical structure in an upper rank than "honeycomb lung" are considered.

Figure 6:
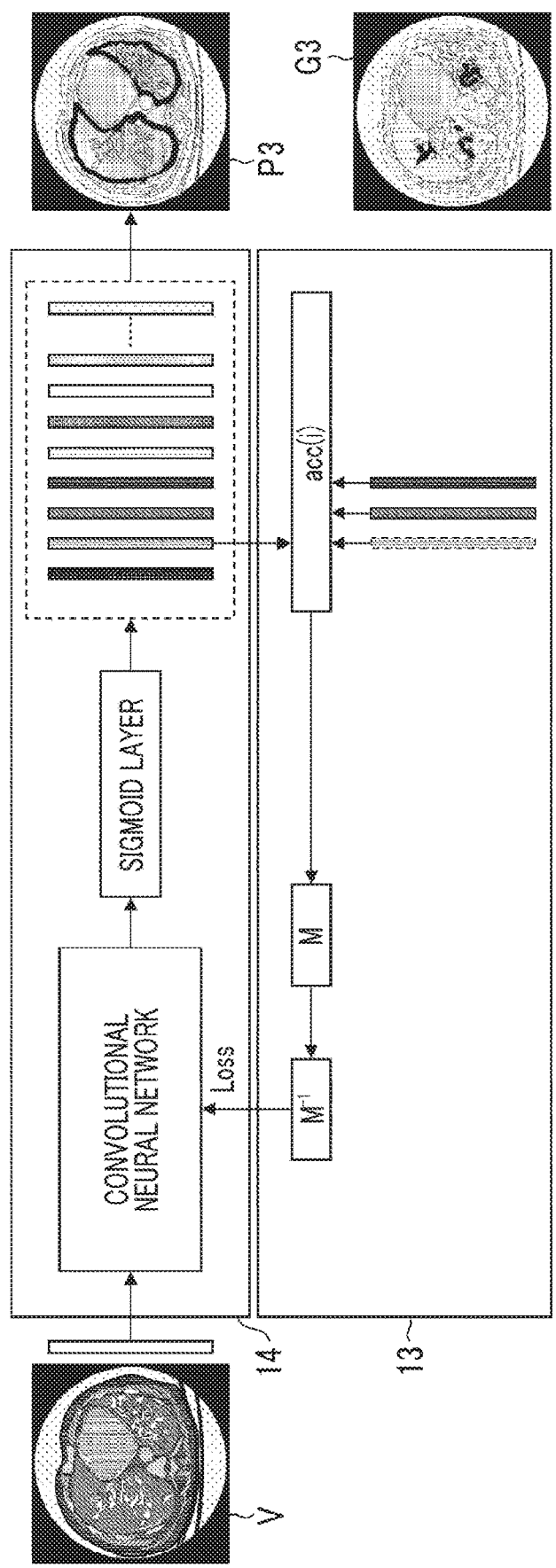
FIG. 6 is a diagram illustrating a concept of backpropagation according to a prediction class (bronchus and blood vessel).

FIG. 6 shows backpropagation due to a learning loss between a ground truth mask G3 of "bronchus" and "blood vessel" and a prediction mask P3 of "bronchus" and "blood vessel" predicted from the volume data V. In this case, backpropagation is performed in which both of learning losses of "bronchus" and "blood vessel" and a learning loss of "lung" of the anatomical structure in an upper rank than "bronchus" and "blood vessel" are considered.

FIG. 7 shows backpropagation due to a learning loss between a ground truth mask G4 of "blood vessel" and a prediction mask P4 of "blood vessel" predicted from the volume data V. In this case, backpropagation is performed in which both of a learning loss of "blood vessel" and a learning loss of "lung" of the anatomical structure in an upper rank than "blood vessel" are considered.

As described above, by collectively performing backpropagation with respect to prediction of an anatomically relevant organ, it is possible to perform efficient multi-labeling machine learning using single-labeled learning data. Therefore, it is not necessary to prepare a large amount of learning data multi-labeled according to anatomically consistent rules. In addition, since backpropagation is performed based on a prediction accuracy, highly accurate multi-labeling is possible.

The present invention can be applied not only to a three-dimensional medical image but also to various two-dimensional images or three-dimensional images. In a case of a two-dimensional image, efficient multi-labeling machine learning using single-labeled learning data can be performed by performing processing in which the voxel described above is replaced with a pixel.

EXPLANATION OF REFERENCES

1: machine learning device
11: learning data input unit
12: relationship data input unit
13: machine learning unit
14: neural network

What is claimed is:

1. A machine learning device comprising:
a first learning data input unit that receives an input of first learning data including volume data of a tomographic image and a ground truth label of a first class in the volume data;
a second learning data input unit that receives an input of second learning data including the volume data and a ground truth label of a second class different from the first class in the volume data;
a prediction label creation unit that, by a neural network, creates a prediction label of the first class from the volume data of the first learning data whose input is received by the first learning data input unit, and creates a prediction label of the second class independent of the prediction label of the first class from the volume data of the second learning data whose input is received by the second learning data input unit;
an integrated error calculation unit that calculates an integrated error between an error between the prediction label of the first class and the ground truth label of the first class and an error between the prediction label of the second class and the ground truth label of the second class by weighted averaging; and
a machine learning unit that causes the neural network to perform machine learning to create the prediction labels of both a label of the first class and a label of the second class in the volume data based on the integrated error calculated by the integrated error calculation unit.

2. The machine learning device according to claim 1, wherein the integrated error calculation unit calculates the integrated error based on an intersection over union (IoU) between the prediction label of the first class and the ground truth label of the first class and an intersection over union (IoU) between the prediction label of the second class and the ground truth label of the second class.

3. The machine learning device according to claim 1, wherein the integrated error calculation unit calculates a detection accuracy based on a Dice coefficient between the prediction label of the first class and the ground truth label of the first class and a Dice coefficient between the prediction label of the second class and the ground truth label of the second class.

4. The machine learning device according to claim 1, wherein the prediction label of the first class and the prediction label of the second class are created based on a sigmoid function.

5. The machine learning device according to claim 1, wherein the tomographic image is a three-dimensional medical tomographic image, and the first class and the second class include an anatomical structure.

6. The machine learning device according to claim 5, wherein the integrated error calculation unit creates the ground truth label of the second class from the ground truth label of the first class based on relevance data indicating a relationship on an anatomical system between the first class and the second class, and then calculates the integrated error between the error between the prediction label of the first class and the ground truth label of the first class and the error between the prediction label of the second class and the ground truth label of the second class.

7. The machine learning device according to claim 6, wherein the second class is in an anatomically upper rank than the first class in the relevance data.

8. The machine learning device according to claim 1, wherein the integrated error calculation unit calculates an integrated error ignoring the error between the prediction label of the first class and the ground truth label of the first class for a region of the volume data in which the ground truth label of the first class does not exist.

9. A machine learning method executed by a computer, the method comprising:
- a step of receiving an input of first learning data including volume data of a tomographic image and a ground truth label of a first class in the volume data;
- a step of receiving an input of second learning data including the volume data and a ground truth label of a second class different from the first class in the volume data;
- a step of, by a neural network, creating a prediction label of the first class from the volume data of the first learning data and creating a prediction label of the second class independent of the prediction label of the first class from the volume data of the second learning data;
- a step of calculating an integrated error between an error between the prediction label of the first class and the ground truth label of the first class and an error between the prediction label of the second class and the ground truth label of the second class by weighted averaging; and
- a step of causing the neural network to perform machine learning to create the prediction labels of both a label of the first class and a label of the second class in the volume data based on the integrated error.

10. A machine-learned model that is machine-learned by the machine learning method according to claim 9.

11. A non-transitory computer-readable recording medium for causing a computer to perform the machine learning method according to claim 9 in a case where instructions stored in the recording medium are read by the computer.

* * * * *